United States Patent [19]

Taylor et al.

[11] Patent Number: 5,170,381

[45] Date of Patent: Dec. 8, 1992

[54] METHOD FOR MIXING AUDIO SUBLIMINAL RECORDINGS

[76] Inventors: Eldon Taylor, 6000 S. Eastern Ave., #9, Las Vegas, Nev. 89119; James R. Woodhams, 3101 LaEntrada, Henderson, Nev. 89014

[21] Appl. No.: 440,244

[22] Filed: Nov. 22, 1989

[51] Int. Cl.[5] .................. H04M 15/00; H04B 1/20
[52] U.S. Cl. ........................ 369/4; 369/1; 381/73.1; 381/104
[58] Field of Search ............ 381/73.1, 104, 1031; 369/1, 3, 4, 292, 84, 85; 358/22, 181, 183; 380/19, 22

[56] References Cited

U.S. PATENT DOCUMENTS

| | | | |
|---|---|---|---|
| 2,825,755 | 3/1958 | Baracket | 358/181 |
| 3,278,676 | 10/1966 | Becker | 358/142 |
| 3,493,681 | 2/1970 | Richards | 369/3 |
| 3,673,324 | 6/1972 | Ito | 358/183 |
| 4,064,364 | 12/1977 | Veale | 369/4 |
| 4,201,895 | 5/1980 | Hill | 369/4 |
| 4,360,114 | 12/1981 | Callahan | 369/3 |
| 4,395,600 | 7/1983 | Lundy | 381/73.1 |
| 4,438,526 | 3/1984 | Thomalla | 381/73.1 |
| 4,551,688 | 11/1985 | Craiglow | 330/280 |
| 4,777,529 | 10/1988 | Schultz | 381/105 |

FOREIGN PATENT DOCUMENTS 2123251  1/1984  United Kingdom ............ 369/1

OTHER PUBLICATIONS

Electronics Today Article, vol. 10, No. 11 (Nov. 1981) p. 57.
Electronics Today Article, vol. 10, No. 12 (Dec. 1981) p. 74.
Schematic Diagram, Tandy Dual Tape Deck, Model #SCT-45-METAL, available from Radio Shack, National Parts Dept. Fort Worth Tex. 76101.

Primary Examiner—Stuart S. Levy
Assistant Examiner—Joseph A. Rhoa
Attorney, Agent, or Firm—John Edward Roethel

[57] ABSTRACT

Audio subliminal recordings are made in which in addition to using a primary carrier, such as music, two audio channels are used to deliver subliminal messages to the brain. On one channel, accessing the left brain hemisphere, the message delivered is meaningfully spoken, forward-masked, permissive affirmations delivered in a round-robin manner by a male voice, a female voice and a child's voice. On the other channel, accessing the right brain, directive messages, in the same voices, are recorded in backward-masked (or meta-contrast). The three voices are recording in round-robin fashion with full echo reverberation. The audio tracks are mixed using a special processor which converts sound frequencies to electrical impulses and tracks the subliminal message to synchronize the subliminal message in stereo with the primary carrier. The processor maintains constant gain differential between the primary carrier and the subliminal verbiage and, with the subliminal verbiage being recorded with round-robin, full echo reverberation, ensures that none of a message is lost. The primary carrier should be continuous music without breaks or great differences in movements.

48 Claims, 14 Drawing Sheets

METHOD FOR MIXING AUDIO SUBLIMINAL RECORDINGS

This application relates to a method and apparatus for mixing audio subliminal recordings, and more particularly to a method and apparatus for mixing audio subliminal recording using a hemispheric approach to send messages to the brain.

BACKGROUND OF THE INVENTION

It is a well-known fact that in a very real sense every human being has two brains, what is termed in everyday speech as a right brain and a left brain, which are actually the right and left hemispheres of the human brain. For the vast majority of people, the left brain hemisphere is in charge of such things as mathematical and language skills while the right brain hemisphere is the creative and emotional center. The left hemisphere is the logic and reason center with defense mechanisms such as rationalization built around logic and reason. The right hemisphere, in contrast, is indiscriminate. Most researchers relate logic and conscious reasoning to the left hemisphere and emotional and subconscious processes to the right hemisphere.

It is thought that the left hemisphere is interested in literal correctness while the right hemisphere is more interested in overall associations and relationships. It is believed that the left hemisphere views language literally and according to the rules of language while the right brain views language spatially and emotionally, tumbling the words in a process called "subconscious cerebration" and even hearing the words as our eyes see the world . . . upside down.

It has been proposed to utilize the way the brain functions by sending the brain subliminal messages. These messages seem to appeal directly to the emotions, causing behavior to override reason. Subliminal messages can be sent either visually or audibly.

In the instance of audio subliminal delivery using audio tapes, a subliminal message can be defined as a verbal stimulus perceived below the threshold of the listener's awareness. Perception in this instance refers to the process of stimuli acknowledged or registered at some level below the threshold of awareness (consciousness). In order for perception by an individual to occur, there must be sufficient stimuli to trigger a neuron in the brain. This is to differentiate from the situation where the message is not only below the threshold of awareness but also is not even perceived, such as a whisper two blocks away from the listener.

In audio subliminal presentation, spoken words are injected beneath a primary carrier. A listener does not consciously hear the spoken words because they are concealed in "white" sound, such as the sound of wind or water, or they are concealed psychoaccoustically in or beneath music. Nevertheless, if appropriately done and the spoken words are not just substantially lowered in volume as compared to the volume of the primary carrier, the stimuli from the spoken words are registered by the listener.

For the sake of an analogy, imagine that the verbal subliminal stimulus rides beneath the waves of nature sounds and music in the same manner as a submarine rides beneath the waves that are on the surface of the ocean. The outer ear catches the sounds (both the surface waves and everything riding thereunder) as they enter the auditory canal. From the auditory canal, the waves are transmitted to the drum membrane, or middle ear, where air pressure and three small bones convey vibrations to the inner ear. Within the inner ear are cochlea, or coiled structures, with sensory cells that receive the sound stimuli and transmit to the brain impulses arising from the sound stimuli. The stimuli ultimately trigger neurons in the brain. Millions of neurons are carrying message units triggered by stimuli across the synapses in the brain and each of these messages is simultaneously competing for conscious attention.

Neurons do not have neutral states; they are either off or on. The threshold of awareness, or "perception level", that exists and is taking place below that threshold is in fact a neural excitation. Without neural excitation, there can be no perception. Research into brain wave activity has confirmed that an increase in pattern activity exists in test subjects who listened to music containing subliminal messages as compared to test subjects listening to the same music without subliminal messages.

The nuances of audio subliminal presentations are widely varied. One process involves "time-compressing" the verbal message by either speeding up the human voice to a high-pitched squeal or by digitally compressing the words, which involves removing the spacing between the sounds which results in one continuous noise.

Another method is known as "multifrequency statements" which involves taking separate messages and overlaying them on different frequencies, then playing all these multi-frequency messages at the same time. Often these multi-frequency messages are recorded at frequencies that an ordinary cassette player cannot reproduce. Audiologists believe such multifrequency messages are imperceptible to humans.

In contrast to these two exotic methods of subliminal message delivery, there are a number of popular and proven methods for delivering verbal subliminal stimuli. One is the concealing of straightforward statements. Another is known as back-masking or metacontrast. A third uses both simultaneously.

In the method of sending subliminal messages known as metacontrast or back-masking, the subliminal messages are recorded in reverse. When subliminal messages are sent to the brain in a reverse or played-backward mode, the subliminal messages appear to excite emotional expressions and responses often viewed as right brain hemisphere in their origin. It is suspected that "heavy metal" recordings have used this process to send satanic, drug or sexual messages to the brain of the listener.

Apparently, the first of the subliminal tracking mixers was developed by Professor Hal Becker of Tulane University in the 1970's. Becker's device, known simply as the "black box", was used to mix spoken words with Muzak. Becker's device was monaural and was tested in a supermarket in New Orleans during 1979. The black box mixed the words "Thou shall not steal" and "Honesty is the best policy" into the Muzak system broadcast throughout the store. This test reportedly achieved a substantial lowering of cash shortages, inventory damage and pilferage.

The electronic mixing of the music (the primary carrier) and the verbal message (the subliminal message) helps ensure a constant signal differential between the two. It is believed that the constant signal differential is critical to the effectiveness of the brain registering the subliminal process.

It is an object of the present invention to provide a method of recording audio subliminal tapes that injects the subliminal verbiage beneath the primary carrier in a manner so that the subliminal verbiage is recoverable (i.e. the presence of the subliminal verbiage on the audio tape is verifiable by electronic means).

It is a feature of the present invention that the subliminal verbiage is injected onto an audio tape beneath the level of the primary carrier at a constant gain differential to ensure effective brain registration of the subliminal verbiage.

It is an advantage of the present invention that the subliminal verbiage injected beneath the primary carrier is effectively perceived by the brain and that the subliminal verbiage is recoverable.

It is a further object of the present invention to provide apparatus for recording recoverable subliminal verbiage beneath a primary carrier at a constant gain differential.

It is a further feature of the present invention that an apparatus is provided that injects subliminal verbiage beneath a primary carrier onto an audio tape combining both forward-masked and backward-masked (or metacontrast) verbiage, including full echo reverberation and round robin verbiage along with multiple voice characteristics.

It is an advantage of the present invention that the apparatus produces a subliminal audio tape recording having recoverable subliminal verbiage which is effectively perceived by the brain.

SUMMARY OF THE INVENTION

The present invention utilizes what is to be called the "whole-brain" approach. In the whole-brain approach, in addition to using a primary carrier, such as music, two audio channels are used to deliver subliminal messages to the brain. On one channel, accessing the left brain hemisphere, the message delivered is meaningfully spoken or sung; forward-masked, permissive affirmations delivered in a round-robin manner by a male voice, a female voice and a child's voice. Research has shown that particular individuals respond more favorably to either a male voice, a female voice or a child's voice depending on the listener's preference. On the other channel, accessing the right brain, directive messages, in the same voices, are recorded in backward-masked (or metacontrast). Since the hemispheres are task oriented, both the right brain hemisphere and the left brain hemisphere become involved according to their individual specialties.

A couple of other nuances may be added. The three voices are recorded in round-robin fashion with full echo reverberation. Split brain studies demonstrate that both the left and right brain hemispheres respond with identification ability to words that are sung. When words are spoken, there are hemispheric limitations that limit the ability of the brain to fully identify and comprehend the words. Further, accelerated learning methods indicate an advantage to the round robin method of communication. The audio tracks are mixed using a special processor which converts sound frequencies to electrical impulses and tracks the subliminal message to synchronize the subliminal message in stereo with the primary carrier.

The processor, to be known as a PAR processor, maintains constant gain differential between the primary carrier and the subliminal verbiage and, with the subliminal verbiage being recorded with round-robin, full echo reverberation, ensures that none of a message is lost.

It is also possible to use as the primary carrier continuous music without breaks or great differences in movements; or; to combine what is known as "white" or "pink" sound, such as ocean surf, with the music. The duration of the breaks in the music must be quite small or the effect of the subliminal messages can be altered.

DETAILED DESCRIPTION OF THE PREFERRED EMBODIMENTS

The initial step is the selection of both the primary carrier and the subliminal verbiage that will be combined to create an audio subliminal recording.

In the preferred embodiment, the primary carrier comprises soothing nature sounds, such as the sound of continuous ocean waves. It is also preferred to use instrumental-only music or to combine such music with the nature sounds. The main criteria is that there should be few, if any, breaks in the primary carrier since the main function of the primary carrier is to hide the verbiage that is being used to convey the subliminal message.

Also in the preferred embodiment, the subliminal message is selected according to certain criteria. For example, positive affirmations in short, compact statements are preferred. If the object of the subliminal message is self-improvement, statements such as "I apply my best" or "I am successful" are used. If the object of the subliminal message is forgiveness, statements such as "I forgive myself" or "I am forgiven" or "I forgive all others" are used.

Also in the preferred embodiment, each such statement is recorded in three different types of voices, such as a man's voice, a woman's voice and a child's voice. In the preferred embodiment, a man's voice is considered to be generally in the range of 540-560 Hz., a woman's voice is considered to be generally in the range of 1000-1050 Hz. and a child's voice is considered to be generally in the range of 950-1030 Hz. This combination of voices in used because listeners tend to respond more favorably to some voice types than to others. The verbiage can either be spoken, sung or a combination of the two since some people respond better to spoken words while others respond better to singing.

An initial recording, usually on tape, is prepared containing the words that will be the subliminal verbiage. Each statement is recorded first in a man's voice, then followed by the same statement in a woman's voice and finally in a child's voice. This same statement may then be repeated or different statements interspersed, each recorded in the three different voices.

Figure 2:
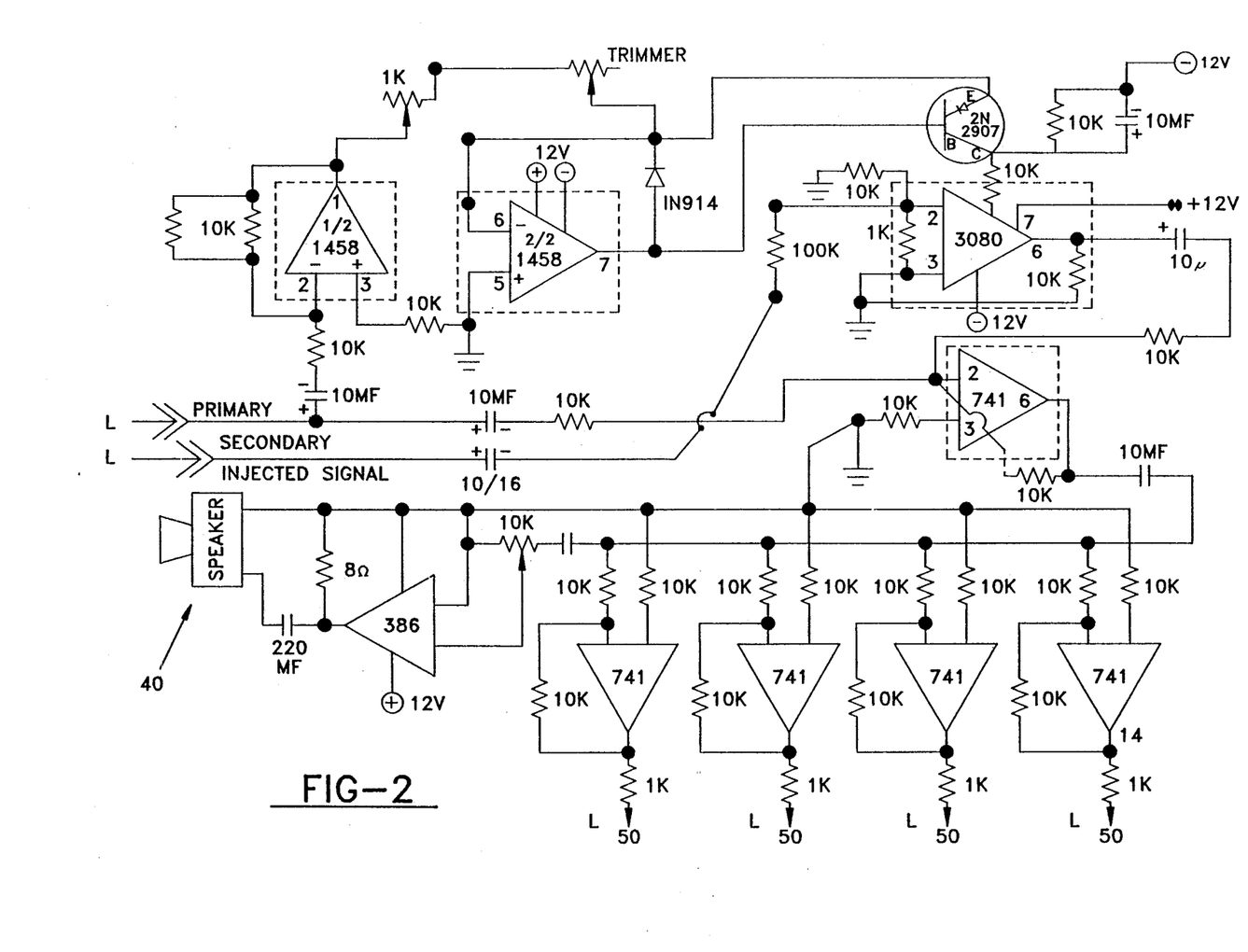
FIG. 2 shows in schematic one of the automatic track mixers of the present invention that mixes the primary carrier with the subliminal verbiage at a constant gain differential.

The initial verbiage that will eventually become the subliminal message on the resulting recording is inputted using the audio mixing device shown in FIG. 2. In the mixing device, the signals from two play heads are played on a first play device, referred to for convenience as Deck #2, and sent through the mixer for further processing. Each play head is loaded with a prerecorded tape having the same verbiage. One of the play heads plays the verbiage in forward play, which will become for example the left channel of the resulting recording, and this verbiage functions as the forward-masked subliminal verbiage in the resulting recording. The other play head plays the verbiage in backward mode which will become the right channel of the resulting recording, and this verbiage is sent through the system for further processing in this backward mode (or metacontrast). When these channels are ultimately recombined, the resulting recording has the same message in both forward and backward mode, but on different channels of the tape.

In addition to this combined forward and backward mixing, three separate play devices may be used—referred to for convenience as Deck #2, Deck #1 and Deck #3. Deck #1 plays the same verbiage as Deck #2, but with a one second time delay. Deck #3 plays the same verbiage as Deck #2, but with a two second time delay. All three decks play the same verbiage both in forward and backward mode. When the signals are combined in the mixer, the result is a round robin effect of the verbiage due to the one and two second time delays of the three decks playing the verbiage.

The left channel of verbiage is all in forward mode and the right channel of the verbiage is in backward or metacontrast mode. Whether forward or backward, each channel has the same message in round robin effect with repeating man, woman and child voices. If desired, full echo reverberation can be electronically added to each channel to prolong the reinforcement of the message contained in the verbiage.

This subliminal message in two channels—the left channel in forward mode and the right channel in backward mode—is then mixed individually with the primary carrier to effect the masking of the subliminal message. The mixing of the subliminal message with the primary carrier is done using the circuitry shown schematically in FIG. 2.

As shown in FIG. 2, the signal from the primary carrier is first sampled for its gain level. By using a variable resistor, the gain level of the primary signal is sampled and the subliminal message signal that is to be injected into the primary carrier is adjusted or varied to be a constant gain differential from the gain level of the primary carrier. In the preferred embodiment, this gain differential is set so that the primary carrier is generally within no more than 20 Db above the gain level of the secondary verbiage or subliminal message signal. In the most preferred embodiment the gain differential is set so that the primary carrier is approximately between 3 Db and 5 Db above the gain level of the secondary verbiage or subliminal message signal.

The adjusted primary carrier signal and the subliminal message signal are then combined and distributed through any suitable distribution means, such as an audio speaker or through distribution preamplifiers for ultimate recording on an audio tape recording device or other suitable recording means as shown in FIG. 2.

FIGS. 1A-1K shows in schematic the dual tape deck used in the system of the present invention. This tape deck is a modification of a dual tape deck made by the Tandy Corporation, National Parts Dept., Fort Worth, Tex. 76101 and sold as Model # SCT-45-METAL. The Tandy dual tape deck is a conventional tape deck which has been modified to suit the purposes of the present invention.

The operation of the modified dual tape deck of the present invention will now be described in connection with explaining the modifications that have been made to the Tandy dual tape deck. A prerecorded tape containing the desired subliminal messages that will be injected as forward masked secondary signals under the primary signal is placed in Tape-1 Play Head and a prerecorded tape containing the desired subliminal messages that will be injected as backward mode or metacontrast secondary signals under the primary signal is placed in Tape-2 Play Head (both shown in FIG. 1A). The prerecorded tape placed in Tape-2 Play Head has the message originally recorded in forward mask mode and one of the modifications made is to reverse the tape heads on the Tape-2 Play Head so that the prerecorded tape played on this head is played backward to provide the backward masking or metacontrast that is to be injected or placed on the resulting subliminal recording. The signal coming from each channel of Tape-1 Play Head and Tape-2 Play Head is pre-amplified and sent through a variable resistor 22A, 22B, 22C and 22D, respectively (shown in FIG. 1C) for individual gain control. This individual gain control is done manually by the operator using the LED indicator circuitry shown in FIG. 4.

Figure 1A:
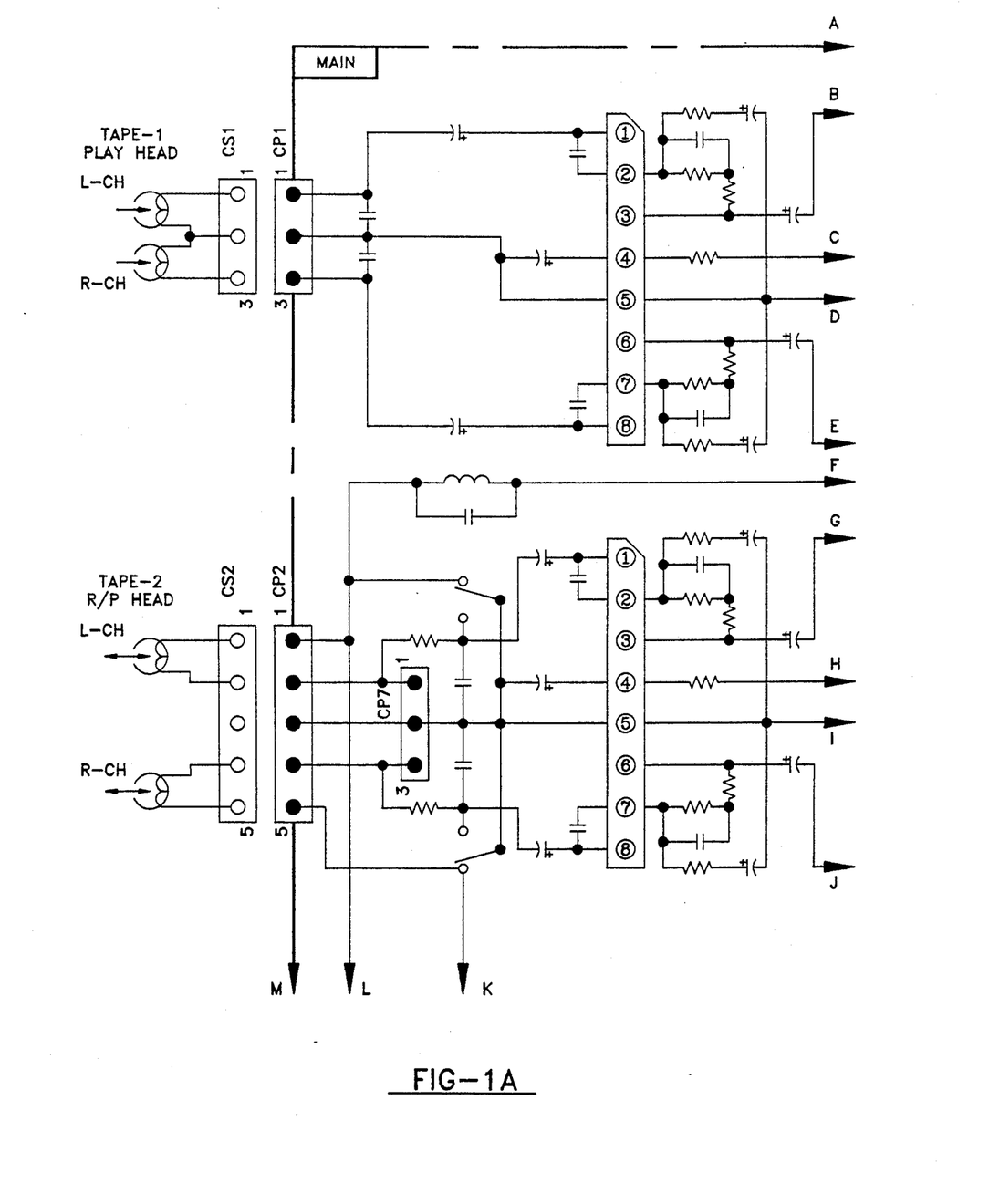
FIGS. 1A-1K show in schematic one of the master audio tape recording decks used in the system of the present invention.
Figure 1B:
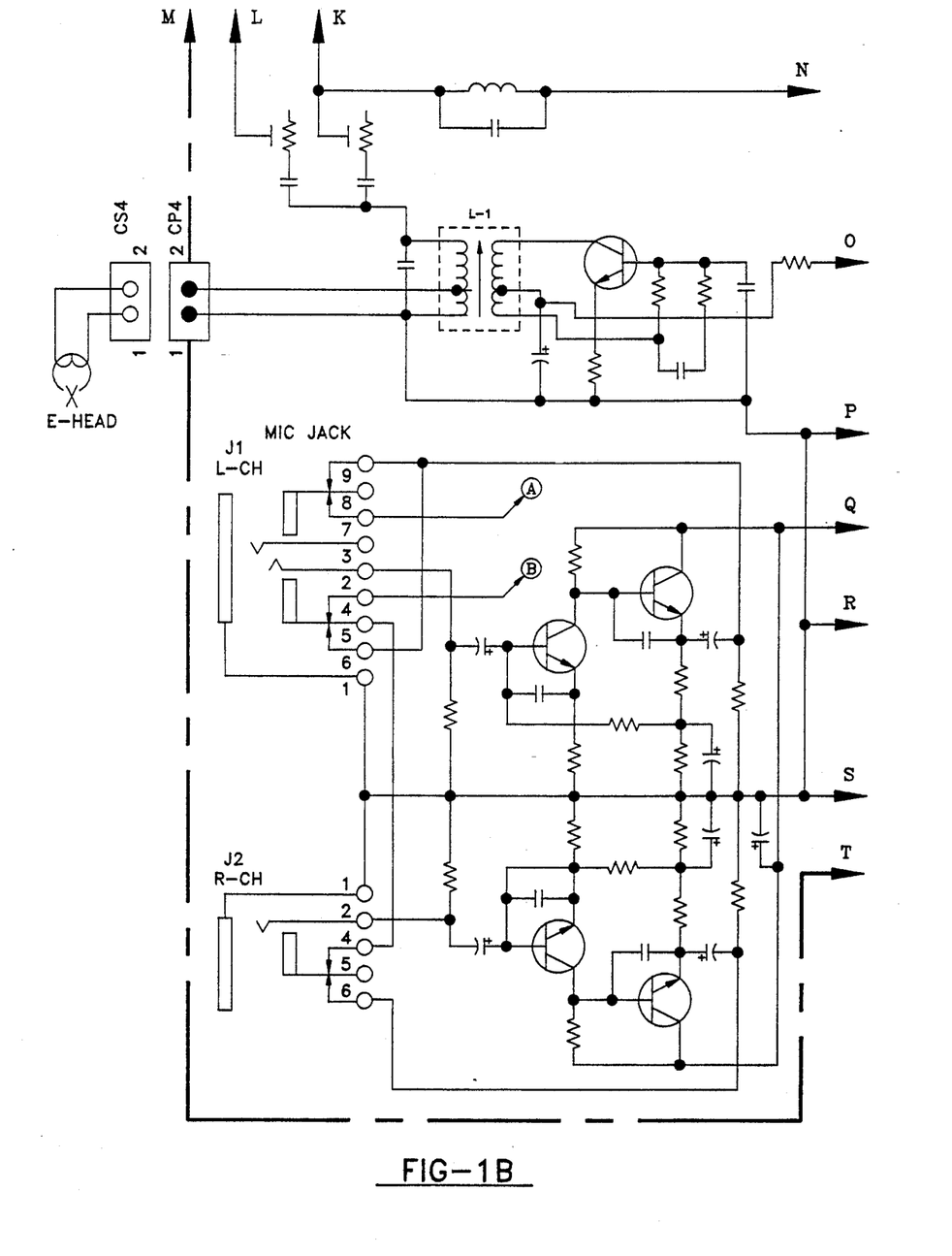
Figure 1C:
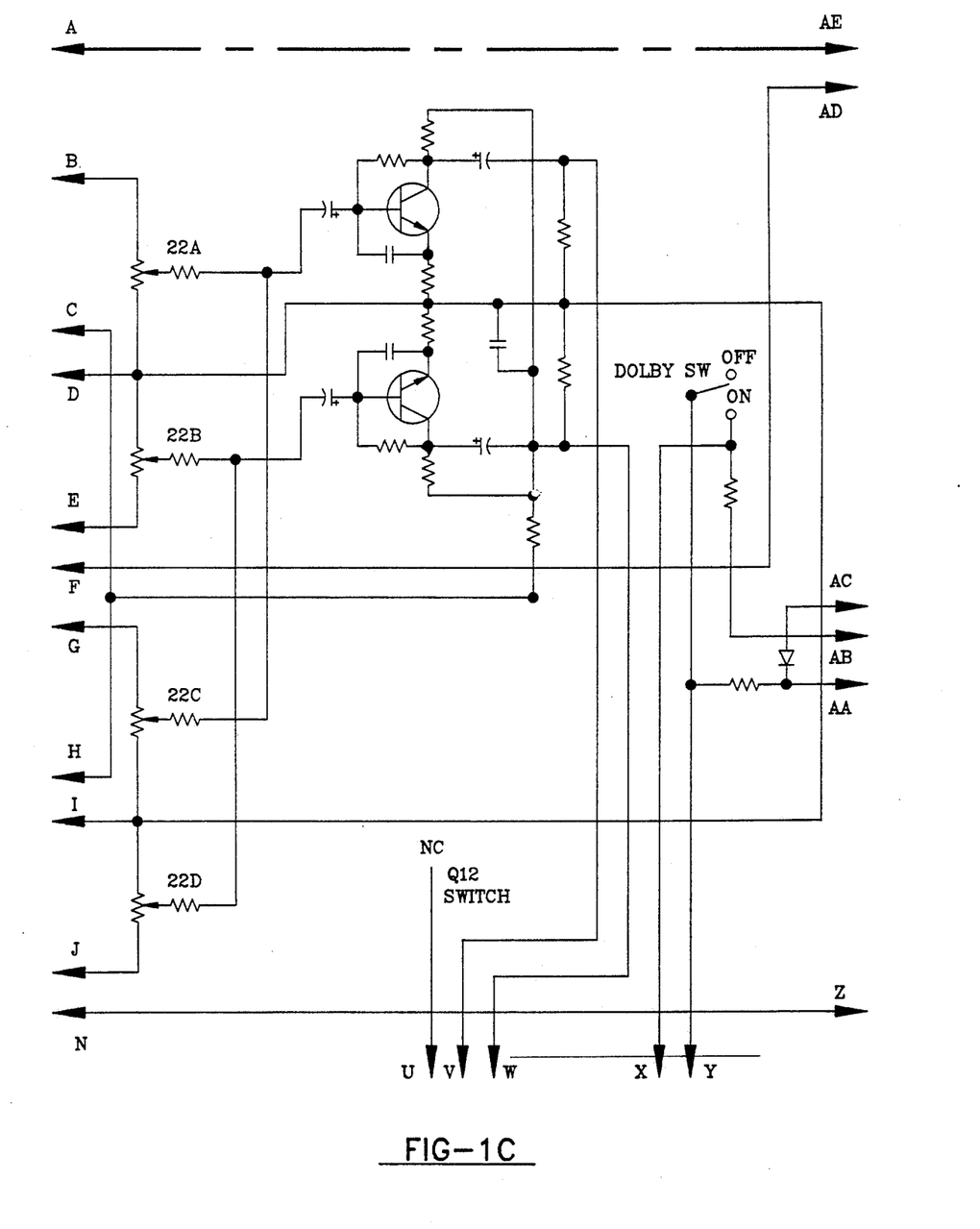
Figure 1D:
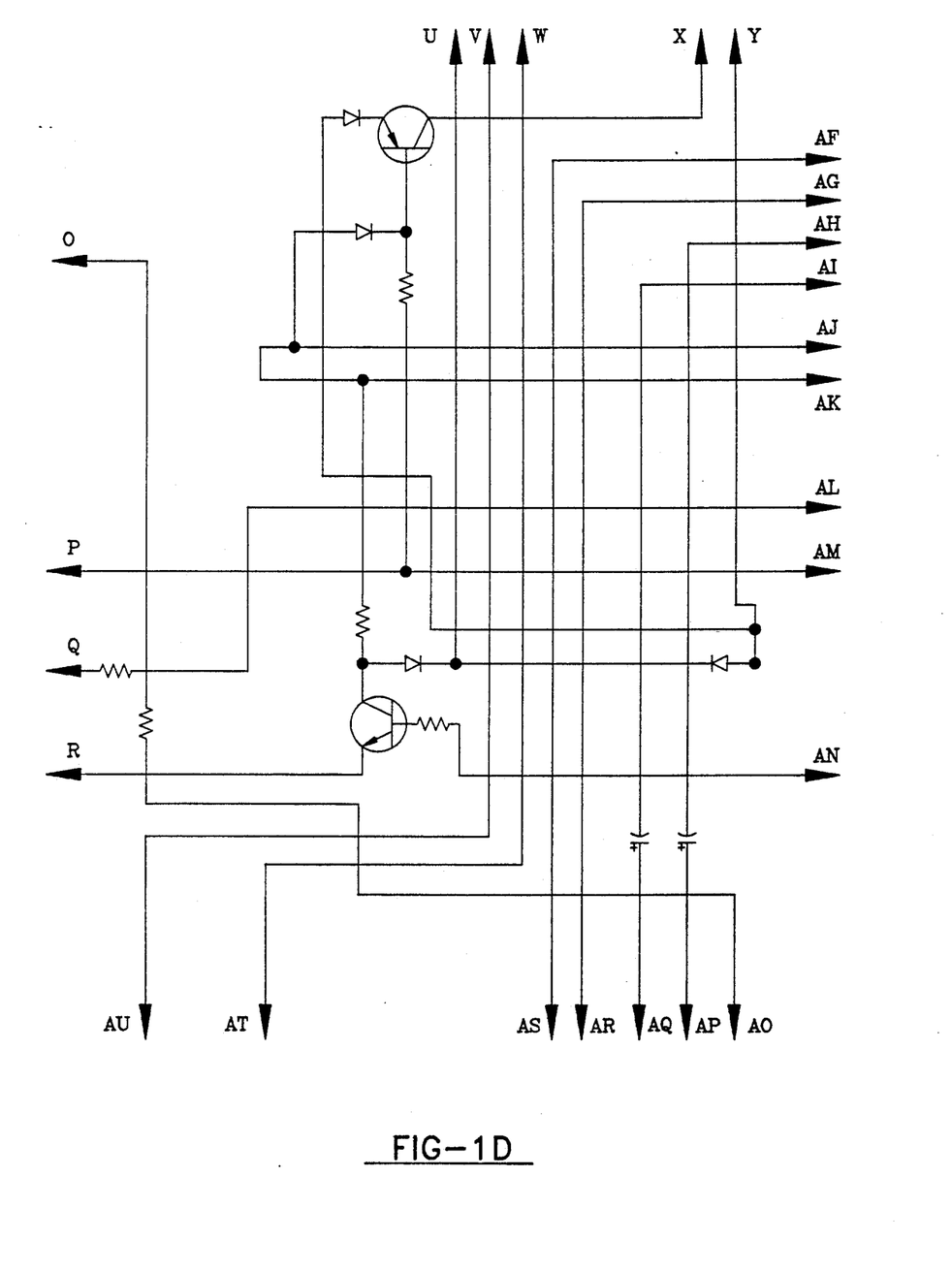
Figure 1E:
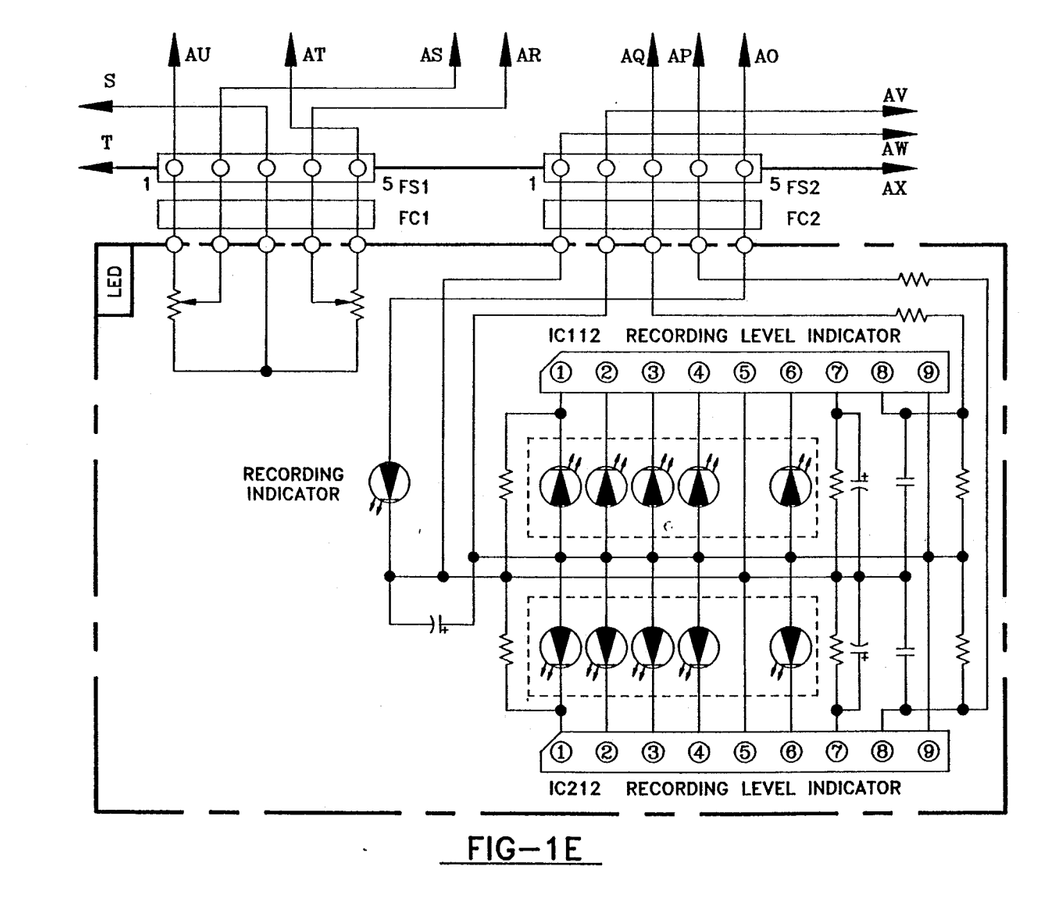
Figure 1F:
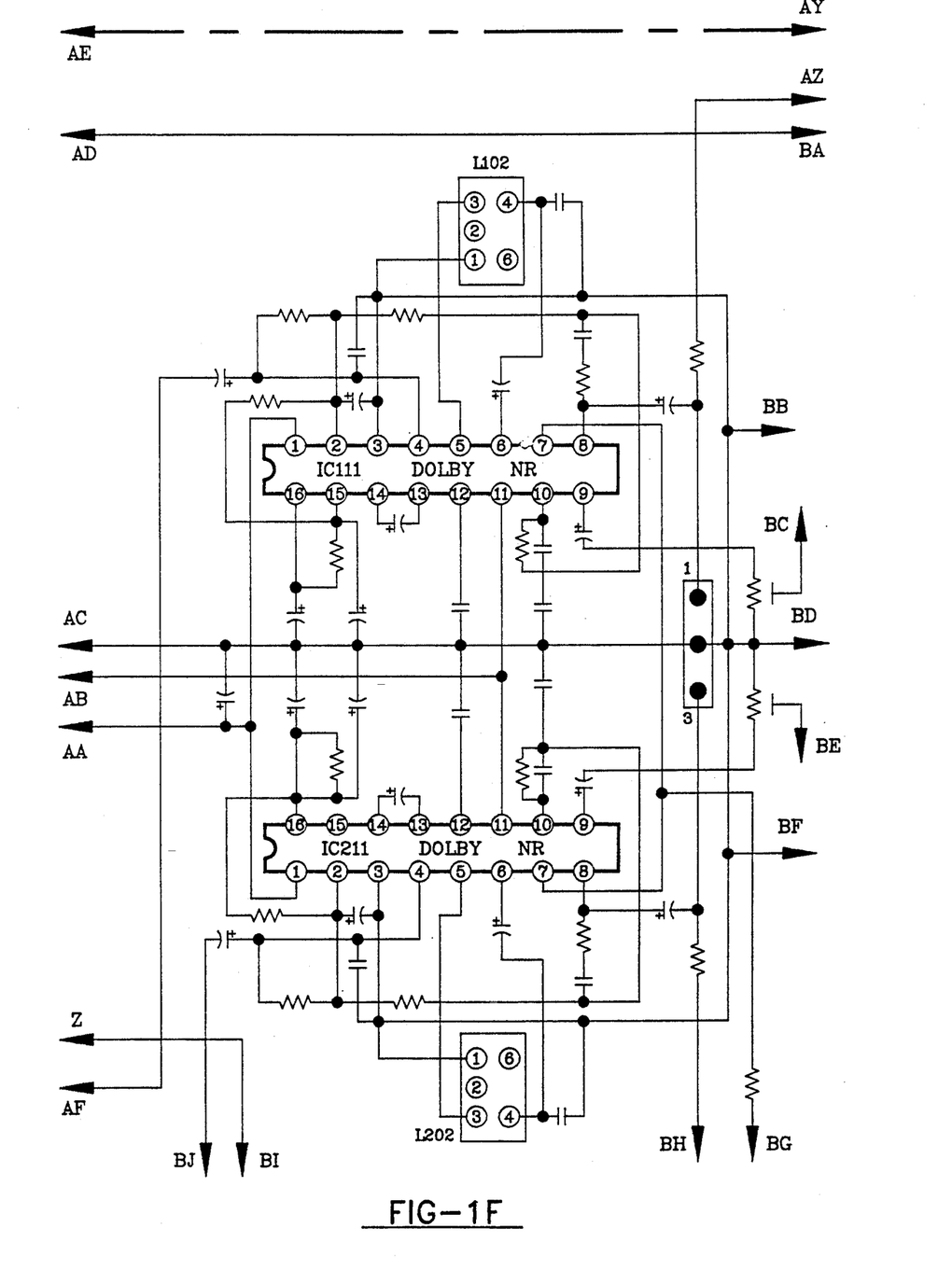
Figure 1G:
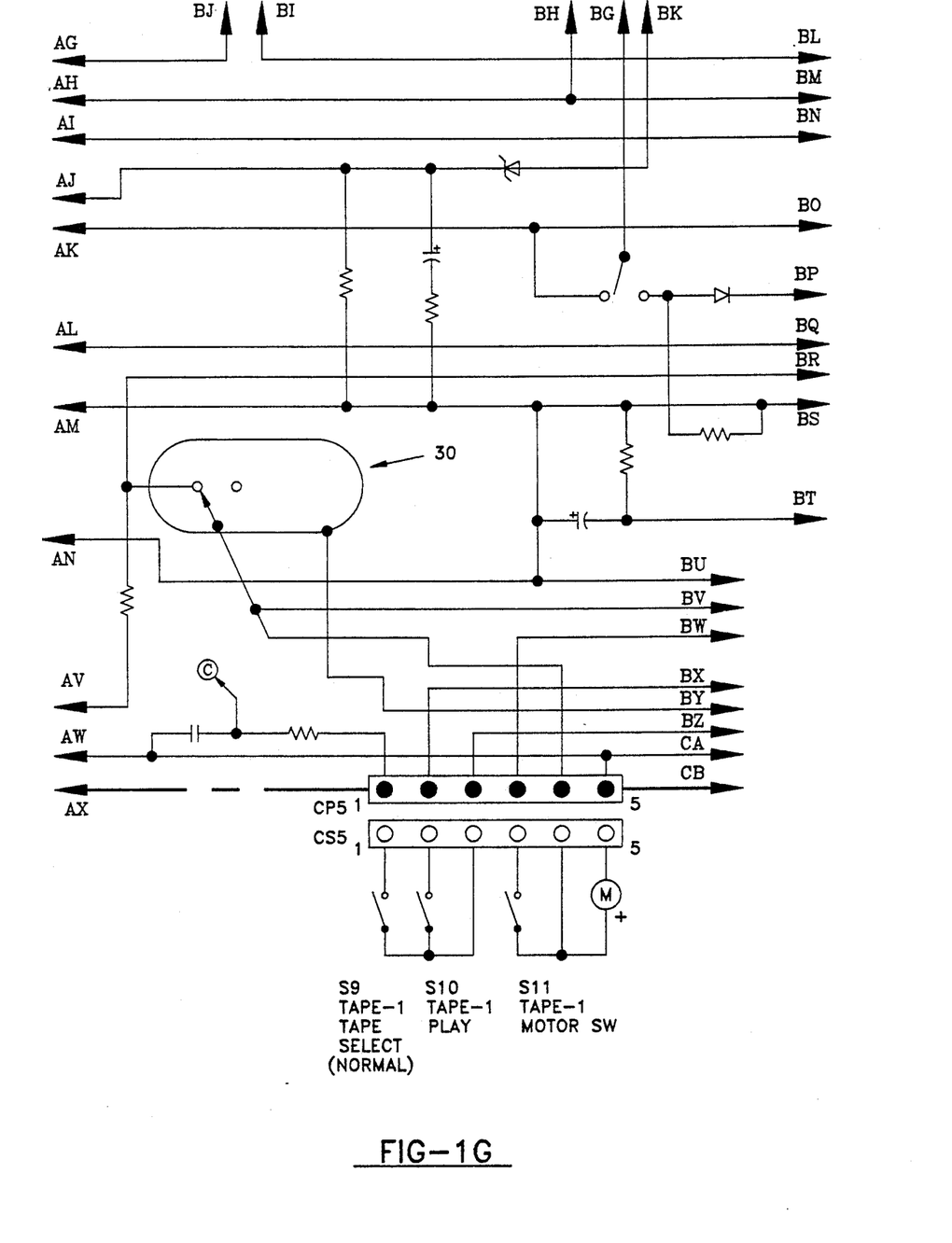
Figure 1H:
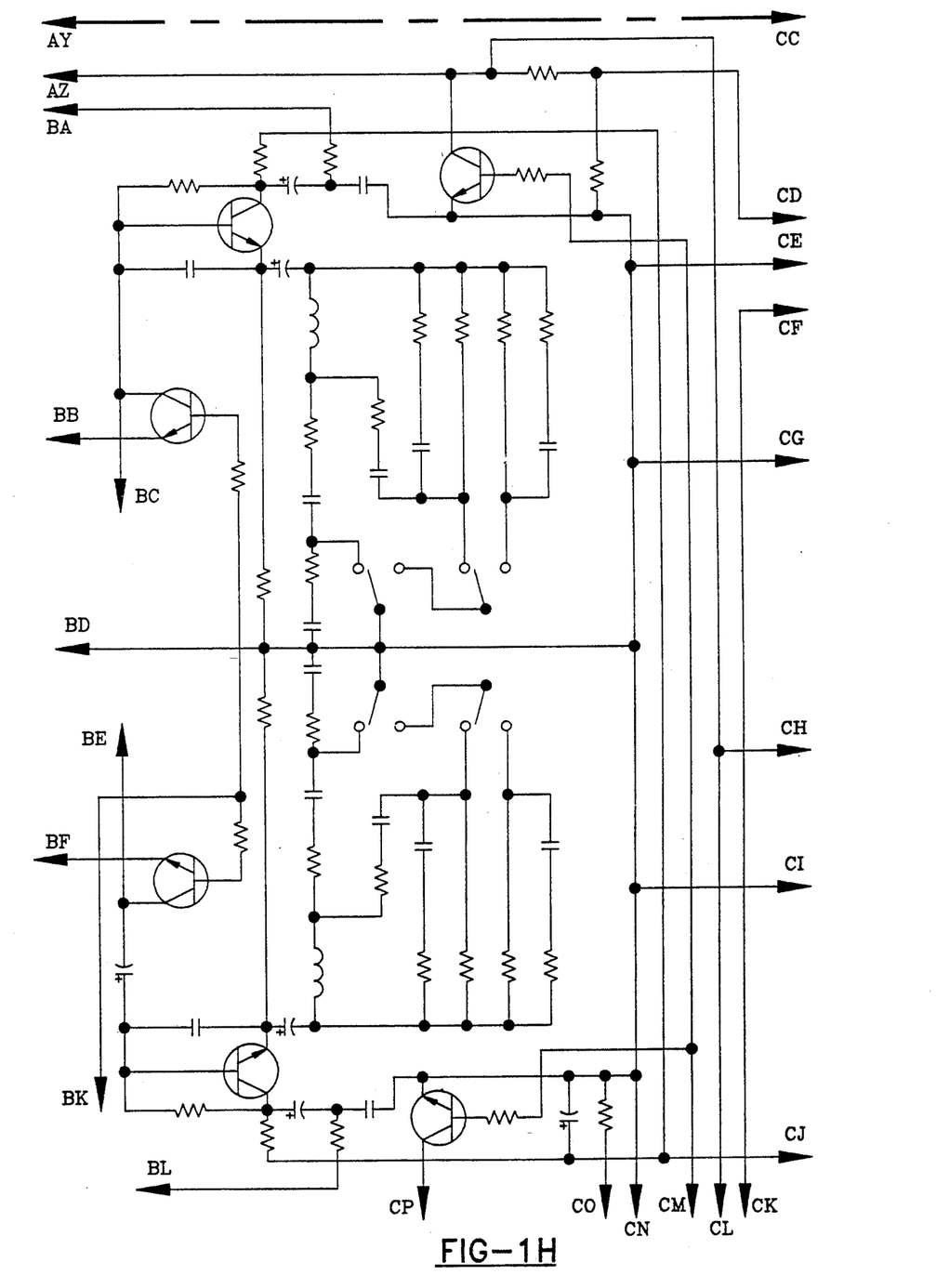
Figure 1I:
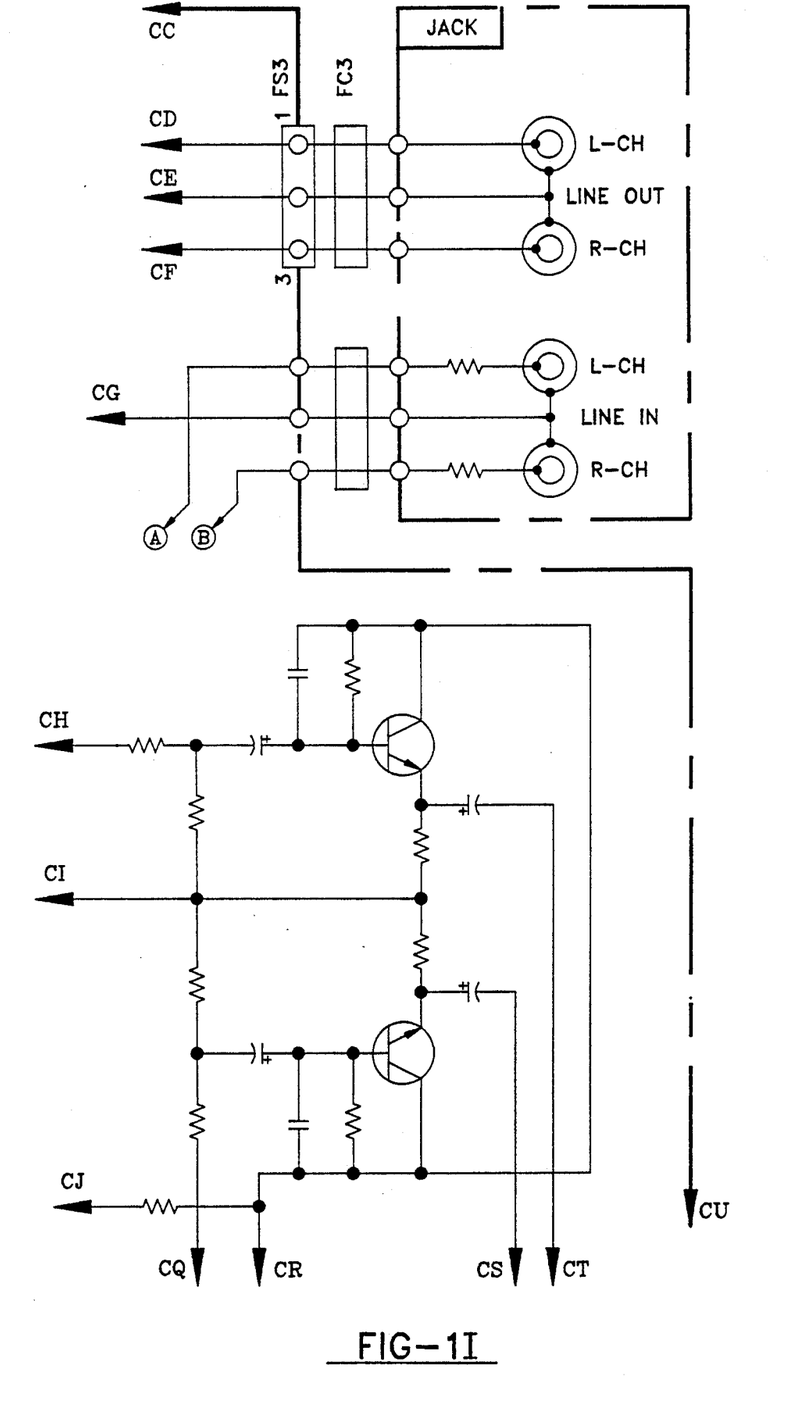
Figure 1J:
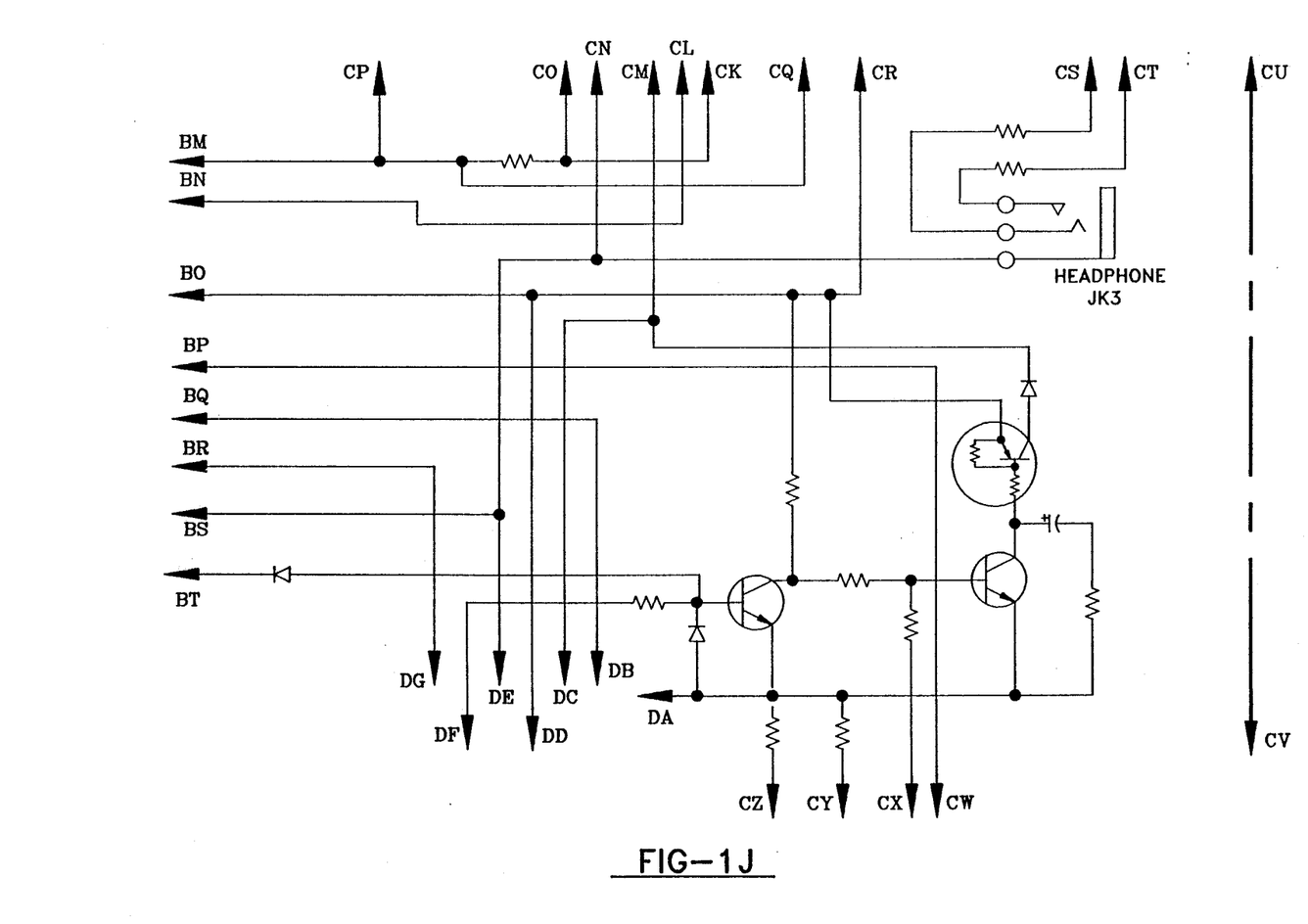
Figure 1K:
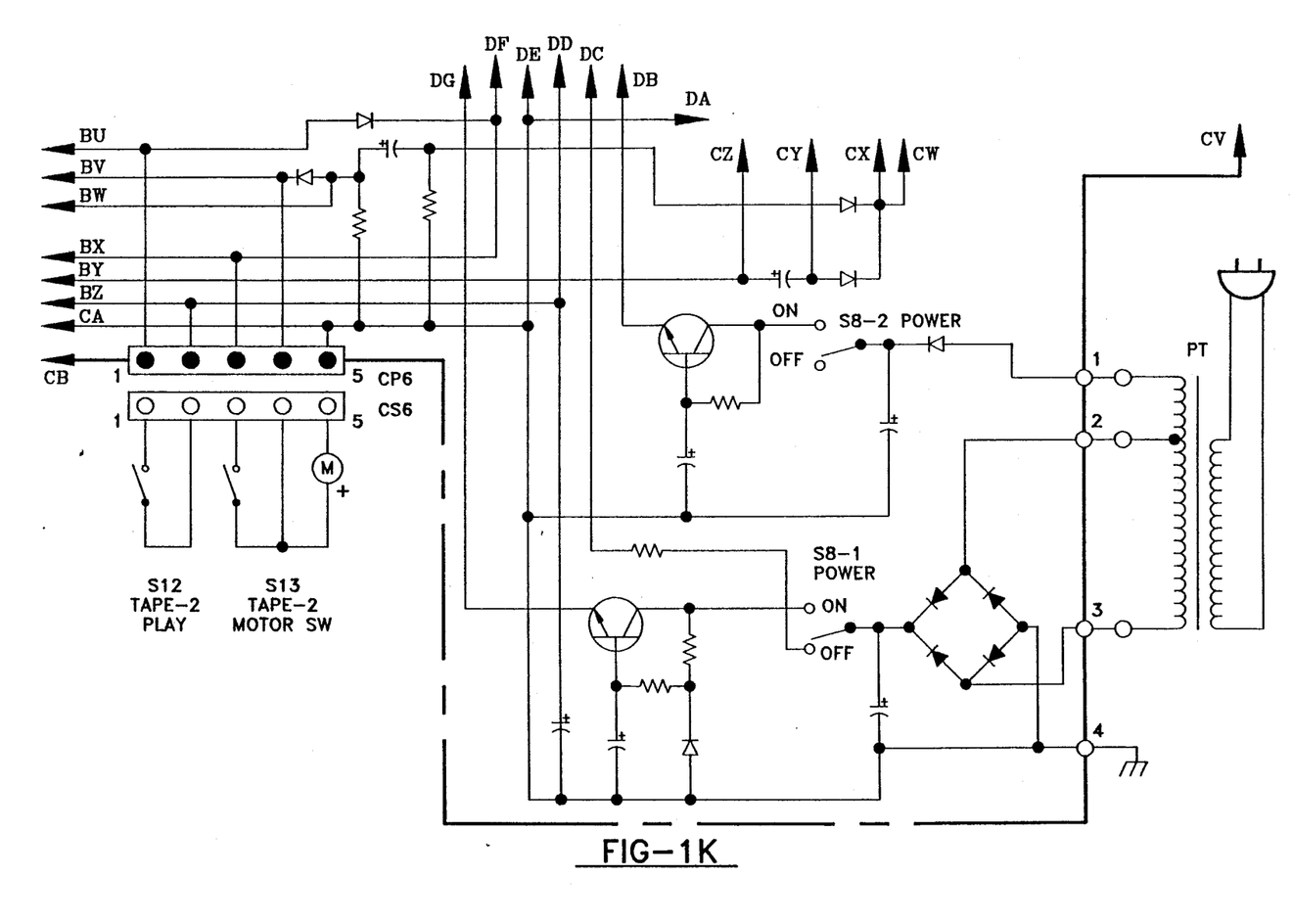

After each signal has been individually adjusted to the proper gain, which in the preferred embodiment is generally within 1 Db of the other signals coming from the other play heads in the tape deck, the signal passes through a Dolby noise reduction circuit shown in FIG. 1F and then pre-amplified for mixing with the primary signal.

One of the other modifications made to the Tandy dual tape deck is that the recording ability of the deck is disabled since the dual tape deck of the present invention is used as a playback unit only. The dubbing capability is also disabled for the same reason. Finally, the tape select switch is modified to become the time delay circuit as will be explained below.

FIG. 2 shows in schematic the automatic track mixer of the present invention that mixes the primary carrier signal with the subliminal verbiage signal at a constant gain differential. As discussed above, the primary signal is soothing nature sounds, such as the sound of continuous ocean waves. It is also preferred to use instrumental-only music or to combine such music with the nature sounds.

As shown in FIG. 2, the primary signal is first continuously sampled to determine its gain level. The secondary signal is continuously combined with the primary signal at a constant gain differential such that the secondary signal is preferably kept generally no more than 20 Db below the gain level of the primary signal and in the most preferred embodiment approximately between 3 Db-5 Db below the level of the primary signal. This prevents the secondary signal from being consciously audible to the listener. The resulting combined signal can then be sent to any one or all of a plurality of output devices such as speakers 40 or through pre-amplifiers 50 for tape recorders (not shown) to make the resulting subliminal audio recording.

As discussed above, in the preferred embodiment, the resulting subliminal audio recording has a channel of forward masked verbiage and a channel of backward masked or metacontrast verbiage. Each channel preferably has three distinct voices—male, female and child—repeating the message in round robin effect with full echo reverberation. As will be described, this is achieved by using various multiples of the apparatus shown in FIGS. 1A-1K and FIG. 2.

Figure 3:
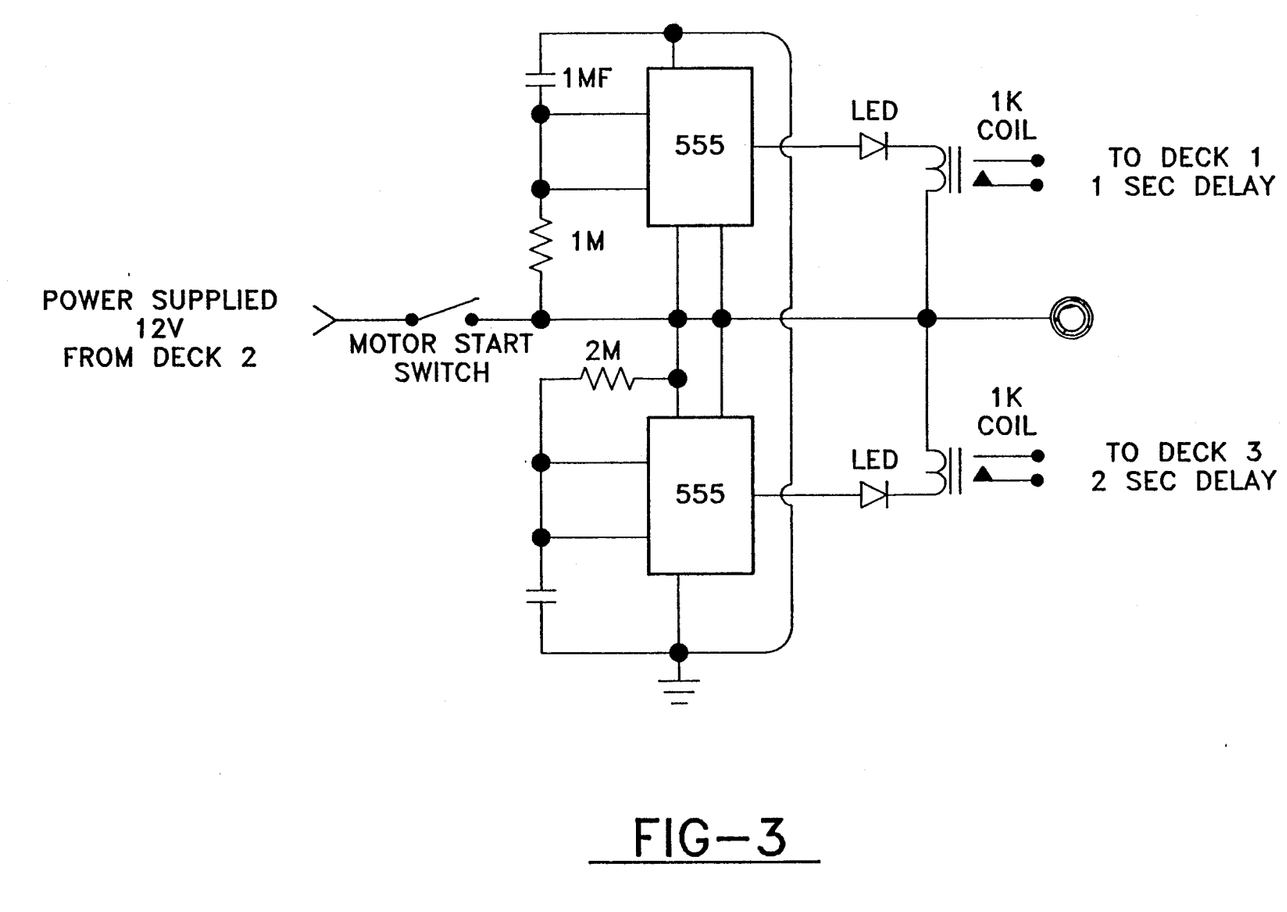
FIG. 3 shows in schematic the time delay circuit used in the system of the present invention.

Three separate dual tape decks, each of the type shown in FIGS. 1A-1K and identified as Deck #1, Deck #2 and Deck #3, are electronically connected together. One of these tape decks, for example Deck #2, is provided with the Time Delay Switch Circuit shown in FIG. 3 (and also shown at 30 in FIG. 1G). Each of Deck #1, Deck #2 and Deck #3 are provided with two prerecorded tapes, one placed in Tape-1 Play Head and one placed in Tape-2 Play Head, containing the verbiage that will be injected onto the primary carrier. Each of Deck #1, Deck #2 and Deck #3 has one of its tape heads (preferably Tape-2 Play Head) reversed so that one of the verbiage tapes will be injected in backward masked or metacontrast mode.

In addition to the three separate dual tape decks, two separate automatic track mixers are used of the type shown in FIG. 2, identified as the Left Mixer and the Right Mixer, since each mixer handles separately all the left channel outputs and the right channel outputs, respectively, from each tape deck.

In operation, after all six of the prerecorded tapes are loaded into the respective Play Heads, the operator activates the system by closing the Time Delay Switch 30 on Deck #2. Deck #2 is activated first and functions as described above. The closing of the Time Delay Switch also activates the Time Delay Circuit shown in FIG. 3. This circuit sends power from the Power Supply to Deck #1 on a one second time delay and then sends power from the Power Supply to Deck #3 after another one second time delay. This delay results in the verbiage from Deck #1 and Deck #2 and Deck #3 being injected onto the primary signal in a round robin and full echo reverberation mode—like what a person would hear if he were listening to verbiage being spoken or sung in round robin.

The outputs from Deck #1, Deck #2 and Deck #3 are sent to one of the two automatic track mixers—all of the three left channel outputs are sent to the Left Mixer and all of the three right channel outputs are sent to the Right Mixer. These three combined signals, forming the round robin effect, are what is injected as the secondary signal onto the primary carrier as shown in FIG. 2. After the automatic track mixer injects the secondary signal onto the primary carrier maintaining the appropriate decibel spacing (preferably not more than 20 Db below the level of the primary signal and most preferably approximately between 3 Db and 5 Db below the level of the primary carrier), the resulting combined signal is recorded on the appropriate track (left or right) of the resulting subliminal audio recording. This results in the primary signal being recorded in stereo providing a very pleasant recording and one that is easy to listen to.

Figure 4:
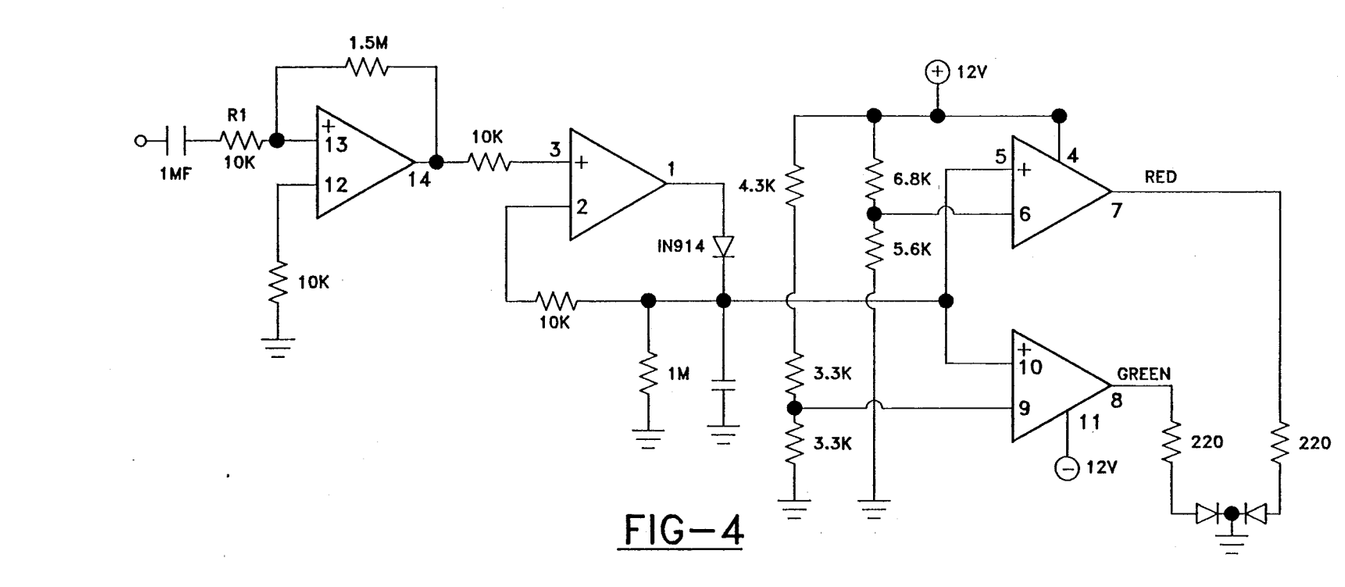
FIG. 4 shows in schematic the circuitry for one of the tri-color LED indicators used in the system of the present invention.

FIG. 4 shows in schematic the circuitry for the tri-color LED indicator used in the system of the present invention. A tri-color LED indicator is attached to each of the variable resistors 22 shown in FIG. 1A. The operator watches the gain level of the signal coming from the play head and manually adjusts the gain level to set the gain level within the desired decibel range as compared to the other gain levels coming from the other play heads. In the preferred embodiment, the gain levels of the various signals coming from the individual play heads should not vary by more than generally one decibel. Rather than having to watch numerical meters, the tri-color LED indicator circuit will illuminate a green light when the particular play head is within one decibel of the desired reference level. If the gain level falls more than one decibel below the desired reference level, the LED is illuminated with a red light alerting the operator that the gain level is too low so that manual adjustment can be made. Similarly, if the gain level rises more than one decibel above the desired reference level, the LED is illuminated with a yellow light alerting the operator that the gain level is too high so that manual adjustment can be made. In the preferred embodiment having Deck #1, Deck #2 and Deck #3, it will be necessary to have twelve of the tri-color LED indicator circuits shown in FIG. 4 since each Deck has four play heads.

Figure 5:
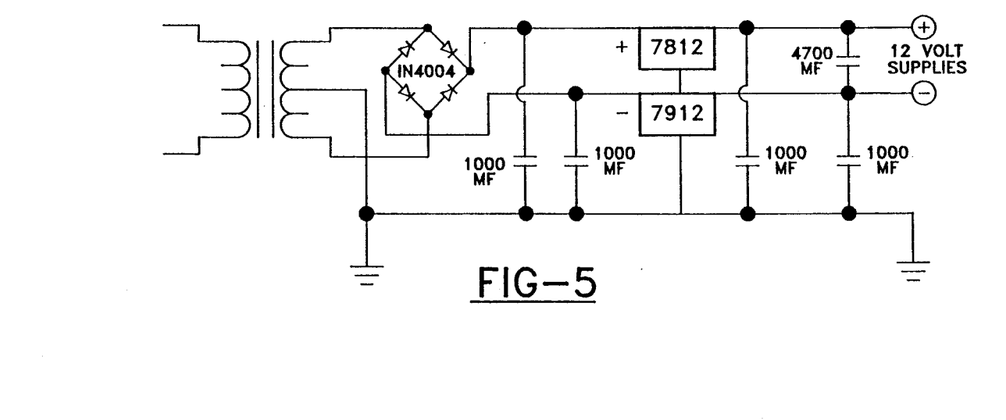
FIG. 5 shows in schematic the power supply used in the system of the present invention.

FIG. 5 shows in schematic the power supply used in the system of the present invention. In the preferred embodiment, the entire three Deck, two Mixer and twelve tri-color LED indicator circuits are operated from a 120 V AC transformer having a 25 V center top. The transformer and accompanying circuit shown in FIG. 5 provides a 12 V power supply to each of the three decks and the attendant peripheral circuits shown in the other Figures. While the invention has been illustrated with respect to several specific embodiments thereof, these embodiments should be considered as illustrative rather than limiting. Various modifications and additions may be made and will be apparent to those skilled in the art. Accordingly, the invention should not be limited by the foregoing description, but rather should be defined only by the following claims.

What is claimed is:

1. A method of making audio subliminal recordings comprising:
   a) selecting a sound to be used as a primary carrier,
   b) selecting verbiage to be injected beneath the primary carrier as a subliminal message,
   c) recording a first statement on a first channel in forward masking form and recording a second statement on a second channel in back-masking form,
   d) combining the first statement on the first channel with the second statement on the second channel to create the subliminal message,
   e) mixing the primary carrier sound with the subliminal message to maintain the volume level of the subliminal message within a constant decibel range beneath the volume level of the primary carrier sound,
   f) recording the mixed primary carrier sound and the subliminal message whereby an audio subliminal recording is created.

2. The method of claim 1 wherein the constant decibel range is generally not more than 20 Db.

3. The method of claim 1 wherein the constant decibel range is not more than approximately 3 to 5 DB.

4. The method of claim 1 wherein the verbiage comprising the first statement is in the form of a positive affirmation and the verbiage comprising the second statement is in the form of a directive message.

5. The method of claim 4 wherein the forward masking statement is a round robin message.

6. The method of claim 5 wherein the round robin message is a three repeat cycle.

7. The method of claim 6 wherein each three repeat cycle comprises a man's voice, a woman's voice and a child's voice.

8. The method of claim 7 wherein the forward masking is in full echo reverberation.

9. The method of claim 4 wherein the forward masking is in full echo reverberation.

10. The method of claim 4 wherein the back-masking statement is a round robin message.

11. The method of claim 10 wherein the round robin message is a three repeat cycle.

12. The method of claim 11 wherein each three repeat cycle comprises a man's voice, a woman's voice and a child's voice.

13. The method of claim 12 wherein the back-masking is in full echo reverberation.

14. The method of claim 11 wherein the back-masking is in full echo reverberation.

15. The method of claim 4 wherein both the forward masking statement and the back masking statement are a round robin message.

16. The method of claim 15 wherein the round robin message is a three repeat cycle.

17. The method of claim 16 wherein each three repeat cycle comprises a man's voice, a woman's voice and a child's voice.

18. The method of claim 17 wherein both the forward masking and the back-masking are in full echo reverberation.

19. The method of claim 15 wherein both the forward masking and the back-masking are in full echo reverberation.

20. An audio subliminal recording made by the method of claim 15.

21. An audio subliminal recording made by the method of claim 4.

22. The method of claim 1 wherein the forward masking and the back-masking messages are different verbiage.

23. The method of claim 1 wherein both the forward masking and the back-masking messages are the same verbiage.

24. An audio subliminal recording made by the method of claim 1.

25. A method of making audio subliminal recordings comprising:
   a) selecting a sound to be used as a primary carrier,
   b) selecting verbiage to be injected at a lower volume level beneath the volume level of the sound of the primary carrier as a subliminal message,
   c) recording a first statement on a first channel in forward masking form and recording a second statement on a second channel in back-masking form,
   d) combining the first statement on the first channel with the second statement on the second channel to create the subliminal message,
   e) continuously sampling the volume level of the sound of the primary carrier,
   f) continuously adjusting the volume level of the subliminal message verbiage to maintain the volume level of the subliminal message verbiage within a constant decibel range below the volume level of the sound of the primary carrier,
   g) mixing the primary carrier sound with the subliminal message verbiage,
   h) recording the mixed primary carrier sound and the subliminal message whereby an audio subliminal recording is created.

26. The method of claim 25 wherein the constant decibel range is generally not more than 20 Db.

27. The method of claim 25 wherein the constant decibel range is not more than approximately 3 to 5 DB.

28. The method of claim 25 wherein the verbiage comprising the first statement is in the form of a positive affirmation and the verbiage comprising the second statement is in the form of a directive message.

29. The method of claim 28 wherein the forward masking is in full echo reverberation.

30. The method of claim 28 wherein the back-masking statement is a round robin message.

31. The method of claim 30 wherein the round robin message is a three repeat cycle.

32. The method of claim 31 wherein each three repeat cycle comprises a man's voice, a woman's voice and a child's voice.

33. The method of claim 32 wherein the back-masking is in full echo reverberation.

34. The method of claim 31 wherein the back-masking is in full echo reverberation.

35. The method of claim 28 wherein both the forward masking statement and the back masking statement are a round robin message.

36. An audio subliminal recording made by the method of claim 35.

37. The method of claim 35 wherein the round robin message is a three repeat cycle.

38. The method of claim 37 wherein each three repeat cycle comprises a man's voice, a woman's voice and a child's voice.

39. The method of claim 38 wherein both the forward masking and the back-masking are in full echo reverberation.

40. The method of claim 37 wherein both the forward masking and the back-masking are in full echo reverberation.

41. An audio subliminal recording made by the method of claim 28.

42. The method of claim 25 wherein the forward masking and the back-masking messages are different verbiage.

43. The method of claim 25 wherein both the forward masking and the back-masking messages are the same verbiage.

44. An audio subliminal recording made by the method of claim 25.

45. The method of claim 28 wherein the forward masking statement is a round robin message.

46. The method of claim 45 wherein the round robin message is a three repeat cycle.

47. The method of claim 46 wherein each three repeat cycle comprises a man'voice, a woman's voice and a child's voice.

48. The method of claim 47 wherein the forward masking is in full echo reverberation.

* * * * *